US006444797B1

(12) United States Patent
Son et al.

(10) Patent No.: US 6,444,797 B1
(45) Date of Patent: Sep. 3, 2002

(54) CHITOSAN MICROFLAKE AND METHOD OF MANUFACTURING THE SAME

(75) Inventors: Tae-won Son, Daegu; Hyun-oh Yoo, Seoul, both of (KR)

(73) Assignee: Ibeks Technologies Co., Ltd., Seoul (KR)

( * ) Notice: Subject to any disclaimer, the term of this patent is extended or adjusted under 35 U.S.C. 154(b) by 40 days.

(21) Appl. No.: 09/710,625

(22) Filed: Nov. 10, 2000

(30) Foreign Application Priority Data

Jul. 18, 2000 (KR) ........................................ 2000-41075

(51) Int. Cl.[7] .............................................. C08B 37/08
(52) U.S. Cl. ........................... 536/20; 536/55; 536/55.1
(58) Field of Search .......................... 514/55; 536/17.2, 536/18.7, 20, 55, 55.1

(56) References Cited

U.S. PATENT DOCUMENTS

| 2,047,218 A | | 7/1936 | Merrill ........................... 91/68 |
| 3,624,201 A | | 11/1971 | Balassa ........................ 424/95 |
| 3,903,268 A | | 9/1975 | Balassa ....................... 424/180 |
| 3,911,116 A | | 10/1975 | Balassa ....................... 424/180 |
| 4,308,377 A | * | 12/1981 | Koshungi .................... 536/20 |
| 4,309,534 A | | 1/1982 | Austin ........................... 536/20 |
| 4,570,629 A | | 2/1986 | Widra ......................... 128/156 |
| 4,572,906 A | | 2/1986 | Sparkes et al. ................ 514/21 |
| 4,833,237 A | | 5/1989 | Kawamura et al. ............. 536/20 |
| 4,833,238 A | | 5/1989 | De Lucca et al. ............. 536/20 |
| 5,035,893 A | * | 7/1991 | Shioya et al. ................ 424/447 |
| 5,093,319 A | | 3/1992 | Higham et al. ................ 514/55 |
| 5,116,824 A | | 5/1992 | Miyata et al. ................. 514/55 |
| 5,599,916 A | | 2/1997 | Dutkiewicz et al. ........... 536/20 |
| 6,124,273 A | | 9/2000 | Drohan et al. ................ 514/55 |

FOREIGN PATENT DOCUMENTS

JP  01152104  *  6/1989  ........... C08B/37/08

* cited by examiner

*Primary Examiner*—James O. Wilson
*Assistant Examiner*—Patrick Lewis
(74) *Attorney, Agent, or Firm*—Cislo & Thomas LLP

(57) ABSTRACT

Disclosed is a chitosan microflake which is exceptionally improved in coatability to the skin. The chitosan microflake is manufactured by dissolving chitosan in a weak acidic, aqueous organic acid solution to give a chitosan solution, extracting chitosan from the solution, and solidifying the solution and pulverizing the form film into the microflake which has a width ten fold greater than thickness. With high coatability onto the skin, the chitosan microflake improves the medicinal efficacies of highly pure chitosan, including wound healing, sterilization, prevention or suppression of cicatrix formation, and recuperation from wounds, upon being applied to external traumas such as dermal damages, surgically operated regions and burns. In addition to the medicine and medical industries, the chitosan microflakes can find numerous applications in a broad spectrum of industries, including food, bioengineering, cosmetic, agricultural, chemical engineering, and environmental industries.

4 Claims, 2 Drawing Sheets

CHITOSAN MICROFLAKE AND METHOD OF MANUFACTURING THE SAME

BACKGROUND OF THE INVENTION

1. Field of the Invention

The present invention relates to chitosan microflakes which are greatly improved in coatability onto the skin. Also, the present invention is concerned with a method for preparing such a chitosan microflake.

2. Description of the Prior Art

Chitin is quantitatively found in the shells of crustaceans, such as crabs and shrimps, and insects, and in the cell walls of fungi, mushrooms and bacteria, and along with potassium carbonate, proteins, lipids, and pigments, serves to support the main structure of the shells and exoskeletons of various animals. Next to cellulose, chitin is the polysaccharide most produced in the world, with as much as ten billion tons of chitin and its derivatives estimated to be produced from living organisms each year.

Despite its abundance in nature, chitin has not been effectively utilized because of its low solubility in aqueous solutions. Owing to this problem, chitin is difficult to form into fibers or films and thus, has found limited applications. In an effort to overcome this problem, chitin was converted into chitosan which is soluble in aqueous acid solutions. A deacetylation technique is generally used for the conversion of chitin into chitosan. Industrially, chitosan, which is water-soluble, is more extensively used than chitin, which is non-water soluble.

Derived from chitin, chitosan, which is an aminopolysaccharide, is known as being bio-friendly, i.e., non-toxic and biodegradable. In addition, chitosan was found to have effective biological activities for use in, for example, cell fusing, tissue culturing and hemorrhage stopping, and biological properties such as antibacterial activity and biocompatibility.

At first, chitin and chitosan were used as coagulants to recover useful materials from the wastewater of food factories. In recent, numerous applications of chitin and chitosan have been found in a broad spectrum of industries, including food, medical and medicine, bioengineering, cosmetic, agricultural, chemical engineering, and environmental industries.

Thus far, wastes from crustaceans, such as crabs and shrimps, have been used as main sources for chitin. In the future, chitin is expected to be obtained from krill. With respect to the production of chitosan, particular attention is paid to fungi because they are found to contain chitosan as well as chitin in their cell walls. Thus, if culture and extraction methods from fungi are developed to ensure the production of the useful polysaccharides, their sources will be expanded.

Typically, chitin is used in an unrefined form for the treatment of wastewater; while refined, high quality chitosan is applied for high value-added fields such as clinical medicine fields and cosmetic fields. Accordingly, there is a strong requirement to develop a method for preparing refined, high quality chitosan at low cost.

U.S. Pat. No. 3,533,940 discloses a method for preparing chitosan from chitin, along with its application to fibers and films. For possible applications, the prepared chitosan is dissolved in aqueous organic solutions. In U.S. Pat. No. 4,699,135, it is disclosed that chitin is dissolved in polar solvents such as lithium chloride-containing dimethyl acetate amide to produce chitin fibers. Also, disclosed is the production of chitosan staples from a solution of chitosan in an aqueous acetic acid solution. U.S. Pat. No. 5,900,479 describes the production of films and fibers of water-insoluble chitin using an aqueous organic acid solution of chitosan.

In addition to these, many other techniques for utilizing chitin or chitosan as raw materials in producing films and fibers are disclosed. In addition, active research has been directed to the production of biocompatible, hygienic products suitable for use in clinical medicine fields and to their possible applications. As a result, various relevant techniques are developed and disclosed at present.

For example, the applicability and superior functionalities of chitin, chitosan and derivatives thereof as materials for use in wound healing agents, artificial skins, pharmaceuticals, blood coagulants, artificial kidney membranes, biodegradable sutures, antibacterial agents, etc. are described in Dynesh et al (Rev. Macromol. Chem. Phys., C40(1), 69–83 (2000)). Another research result can be referred to Maryefan et al (ILEE Engineering In Medicine and Biology November/December, 1999), reporting that bedcovers with a coating of chitosan have the medicinal effects of preventing the formation of cicatrices and facilitating wound healing.

Recently, there have been reported various research results concerning chitosan's activities against tumors and cancers. In addition, chitosan has been, in a variety of routes, examined for the mechanism for improving the wound healing capability of the body. According to a generalized hypothesis, positively charged ions of chitosan are combined with negatively charged ions of bacteria to agglutinate the bacterial cells to inhibit them from transferring into other tissues or regions than the original lesions, thereby improving the wound healing capability of the body. Chitosan is slowly hydrolyzed by enzymes in vivo, but easily degraded into oligomers and dimmers by lysozyme, which exists in abundance at wound sites of the skin. These hydrolysates are known to continuously exert medicinally healing actions on the wounds for a long period of time.

Known as the first patents concerning use of chitin and chitosan in wound healing agents, Germany Pat. Nos. DE 1906155 and DE 1906159 disclose the medicinal efficacy of chitin or chitosan powder on wound healing. A similar content can be found in British Pat. No. GB1252373.

U.S. Pat. Nos. 3,632,754 and 3,914,413 teach that chitin has the effect of facilitating wound healing and can be physiologically solubilized by virtue of its hydrolysis by lysozyme.

In both European Pat. No. EP0089152 and Japanese Pat. No. 86141373, there is disclosed that composite films prepared from chitin and keratin or collagen are used as wound protectives.

As described above, there are many techniques for applying chitin and chitosan for medicinal purposes. However, most of the conventional techniques only suggest the availability of chitin or chitosan as biocompatible materials, but failed in their commercialization. Further, nowhere is mentioned the preparation of chitin and chitosan into forms which can be properly applied for various clinical-pathological treatments with maximal functionality.

Skins of the body assume various forms, depending on body regions. With exercise, skin differs from one body region to another in physical properties such as extension and contraction extent. For these reasons, there is a strong requirement for a novel form of chitosan, which is greatly improved in coatability. Because conventional chitosan applications for skins are in the form of powders, films, sponge or sheets, an extreme limitation is imposed on their uses.

For instance, chitosan powders are difficult to uniformly apply onto a dermal wounded region. To this end, a large quantity of chitosan powder is required. Another disadvantage of chitosan powder is that chitosan powder is too small in contact area with the dermal region to sufficiently exert its medicinal effect. Also, chitosan powder is poor in close adherence. As for chitosan films, sponge or sheets, they suffer from disadvantages of having difficulty in closely adhering to skins and being extremely limited in size. Furthermore, it is expected that they are not able to maintain close adherence to the skin, which continuously conducts movements such as extension and contraction.

SUMMARY OF THE INVENTION

Therefore, it is an object of the present invention to overcome the above problems encountered in prior arts and to provide a method for preparing chitosan into microflake forms which are exceptionally improved in coatability to the skin.

It is another object of the present invention to provide chitosan microflakes which have very high coatability onto the skin, thereby improving the medicinal efficacies of highly pure chitosan, including wound healing, sterilization, prevention or suppression of cicatrix formation, and recuperation from wounds, upon being applied to external traumas such as dermal damages, surgically operated regions and burns.

The chitosan microflakes of the present invention are manufactured by dissolving chitosan in a weak acidic, aqueous organic acid solution to give a chitosan solution, extracting chitosan from the solution, and solidifying the chitosan into anisotropic microflakes which have widths ten fold greater than thickness.

When being applied onto skin, the chitosan microflakes of the present invention form a mosaic plane, thereby exhibiting greatly improved coatability onto the skin. In addition, the chitosan microflakes adhere so well to the skin as to maximize their medicinal function.

The chitosan microflake structures provided according to the present invention, which are novel forms which have not been manufactured before the present invention, can be effectively used as clinical-pathological agents with high coatability onto skin and maximize the medicinal efficacy of chitosan.

DETAILED DESCRIPTION OF THE INVENTION

Figure 1:
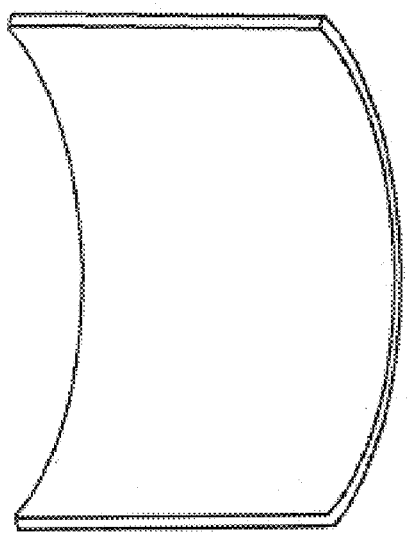
FIG. 1 is a schematic view showing a structure of a chitosan microflake according to the present invention.

The present invention contemplates a novel form of chitosan, which is greatly improved in coatability onto skin and maximizes the medicinal efficacy of chitosan. The novel form is found to be microflakes in accordance with the present invention. The microflakes are prepared by dissolving chitosan in a weak-acidic solvent in a particular weight ratio, freeze-drying the solution, extracting the dried chitosan into porous chitosan films, and pulverizing the films into microflakes in which the width is at least 10 times greater than thickness.

Suitable in the present invention are chitosan which ranges in polymerization degree from 20 to 10,000 and in deacetylation degree from 60 to 99%. More preferable is chitosan which ranges in polymerization degree from 100 to 5,000 and in deacetylation degree from 70 to 95%. Any solvent may be used if it is selected from aqueous acidic solutions, aqueous inorganic salt solutions and organic solvents.

To obtain an aqueous acidic solution available in the present invention, water is added with 0.1–20 wt% of an acid which is selected from the group consisting of organic acids, such as acetic acid, lactic acid, citric acid, tartaric acid, malic acid, formic acid, glycolic acid, oxalic acid, succinic acid, ascorbic acid, maleic acid, acrylic acid, gluconic acid, glutamic acid and propionic acid; inorganic acids, such as hydrochloric acid, sulfuric acid, and phosphoric acid; and mixtures thereof.

Available inorganic salt solutions contain an inorganic salt at an amount of 10–70 wt % in water. The inorganic salt is selected from the group consisting of sodium thioisocyanate, zinc chloride, calcium chloride, sodium chloride, potassium chloride, lithium chloride, and mixtures thereof.

Useful organic solvents in the present invention are polar, examples of which include dimethylacetamide, N-methylpyrrolidone, dimethylformamide, diethylacetamide, trifluoroacetic acid, trichloroacetic acid, methylene chloride, tetrachloroethane and mixtures thereof. In order to obtain higher polarity, one or more selected from the above-mentioned inorganic metal salts may be added at an amount of 1–10 wt % to the organic solvent.

In the selected solvent, chitosan is dissolved at 0.5–30 wt % to give a chitosan solution which is then subjected to freeze-drying and pulverization to produce chitosan microflakes.

Generally, freeze-drying can be achieved by freezing a material and drying the material through direct sublimation under high vacuum without undergoing a liquid phase. Over ordinary drying techniques, the freeze-drying technique has the advantage of producing higher quality products. In addition, freeze-dried products are characterized in that they are of slightly porous structures. In fact, freeze-drying techniques are applied for the manufacture of food and medicines and the drying of microorganisms to afford higher quality products.

In the present invention, the freeze-drying is carried out in three steps: pre-freezing, sublimation-drying, and dehydration-drying.

Because of its a great influence on the final product, the freezing temperature of the pre-freezing must be carefully controlled. In the present invention, the chitosan solution is pre-frozen at a temperature from –10° C. to –60° C. and more preferably at a temperature from –35° C. to –40° C.

In the sublimation-drying step, the frozen chitosan solution is deprived of the free solvent which corresponds to 65 wt %–90 wt % of the total solvent present in the frozen chitosan solution. In this regard, heating and sublimating processes are repeated at regular time intervals while the is latter is conducted at a temperature from –10° C. to –60° C. for 10 min to 2 hours under a pressure of 100 Torr to 0.1 Torr.

In the dehydration-drying step, the combined solvent which is present at an amount of 10–35 wt % of the total solvent in the sublimated chitosan solution is removed. To this end, heating is conducted such that all calories are consumed for the sublimation phase transition from the frozen phase. Therefore, the moisture is gradually removed from the top of the frozen phase while a porous structure of a chitosan film appears. As the level at which sublimation occurs travels downward, the porous structure becomes greater. At last, the frozen phase disappears while a porous chitosan film is obtained.

Afterwards, the porous chitosan film is freeze-pulverized at a temperature of 0° C. to −60° C., followed by passing the pulverized chitosan film through a sieve of 10–100 meshes to give highly pure microflakes which have widths at least ten fold larger than the necessary thickness.

With reference to FIG. 1, there is a schematic view of a chitosan microflake whose width is ten or more times as great as its thickness.

As described hereinbefore, prior arts suggest fiber, film or powder forms of chitosan as medicinally useful coatings, but these are proven to be unable to maintain close adherence to the skin and thus, cannot effectively exert the medicinal effects of chitosan on the skin. In contrast, having an anisotropic morphology in which the width is ten or more times as large as the thickness, the chitosan microflakes of the present invention can be brought into close contact with the skin so that they can improve the medicinal effects of chitosan. That is, when applied onto dermal wounds, such as cuts, surgically operated dermal regions, burns, etc., the chitosan microflakes of the present invention show anti-inflammatory activity, facilitating the healing of the wounds. For this healing, the chitosan microflakes effectively perform the functions of fortifying the connective tissues, moisturizing the wounded skin to an appropriate extent, and ensuring the maintenance of the activity of chitosan.

A better understanding of the present invention may be obtained in light of the following examples which are set forth to illustrate, but are not to be construed to limit the present invention.

EXAMPLE 1

Preparation of Chitosan Solution

In 95 g of an aqueous 3 wt % lactic acid solution was dissolved 5 g of chitosan which was 116 cps in viscosity with a deacetylation degree of 94% to give a transparent solution.

Pre-Freezing Treatment

The chitosan solution thus obtained was placed in a container of a freeze-drier and-frozen at as low as −50° C.

Sublimation-Drying and Dehydration-Drying Treatment

The pre-frozen chitosan solution was subjected to freeze-drying at a pressure of 0.1 Torr for 2 hours while the temperature was changed from −5° C. to 50° C. As a result, porous chitosan films were obtained.

Production into Chitosan Microflakes

Using an electrical pulverizer, the freeze-dried, highly pure, porous chitosan film was pulverized at −30° C. for 10 min to produce chitosan microflakes in which the width was at least ten fold larger than the thickness.

Figure 2:
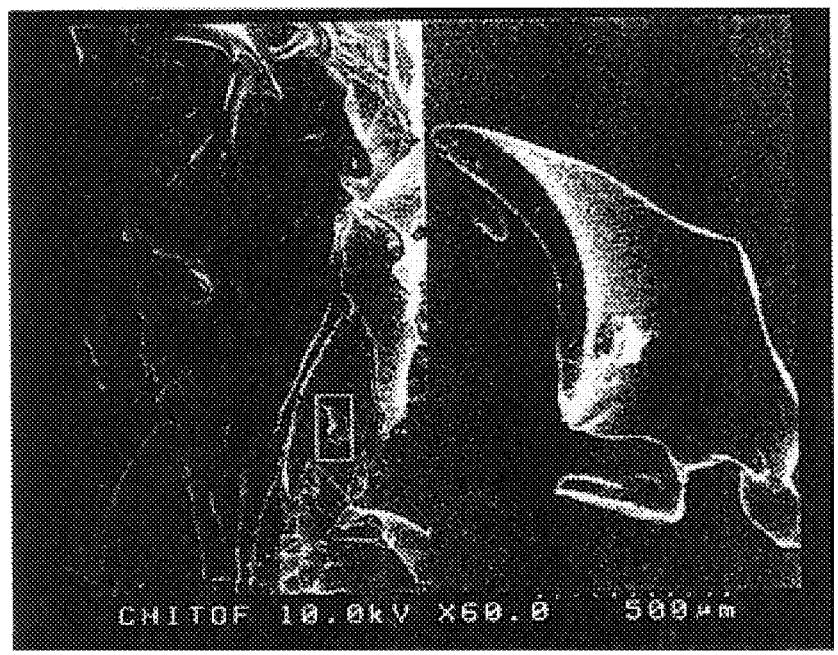
FIG. 2 shows chitosan microflakes at a magnification of 60 times (left) and at a magnification of 6,000 times (right)

The morphologies of chitosan microflakes of the present invention are shown in the microphotographs of FIG. 2. As seen in FIG. 2, the microflakes have wide plate structures whose widths are greater than the thickness. The left microphotograph shows aggregated chitosan microflakes at a magnification of 60 times while the right microphotograph further magnifies a portion of the left microphotograph at 100 times and thus, shows a chitosan microflake in a total magnification power of 6,000 times.

Figure 3:
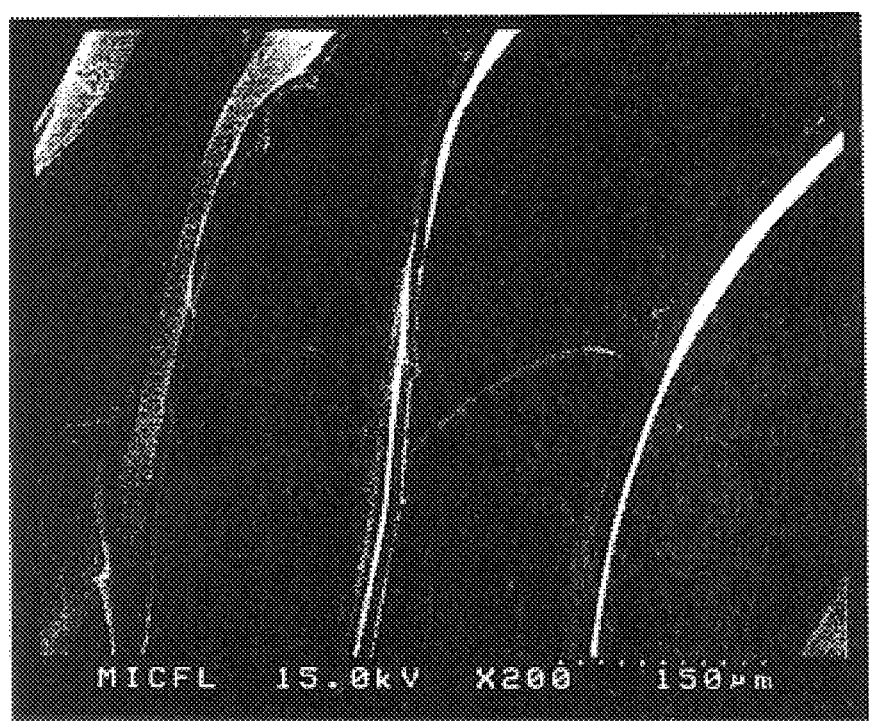
FIG. 3 is a scanning electron microphotograph (SEM) of a freeze-dried chitosan microflake, magnified by 200 times.

Turning to FIG. 3, there is an SEM of a freeze-dried chitosan microflake, magnified by 200 times. As demonstrated in the electron microphotograph, the chitosan microflake has a plate structure.

EXAMPLES 2 TO 5

Properties of Microflakes According to Chitosan

The same procedure of Example 1 was repeated with the exception that 3 g of each of chitosans which had viscosities of 11.6, 116, 370, and 1,446 cps, respectively, all being deacetylated at 94%, and an aqueous 5 wt % lactic acid solution were used, so as to form chitosan microflakes in which the width was at least ten folds larger than the thickness.

Ten chitosan microflakes selected randomly from each of Examples 2 to 5 were measured for dimension and their average values are given in Table 1, below.

TABLE 1

| Properties of Chitosan | Nos. of Examples | | | |
|---|---|---|---|---|
| | 2 | 3 | 4 | 4 |
| Chitosan Viscos. (cps) | 116 | 116 | 370 | 1146 |
| Avg. Thick. of Microflakes | 1.1 μm | 1.3 μm | 1.3 μm | 2 μm |
| Avg. Width of Microflakes | 11.2 μm | 42 μm | 49 μm | 63 μm |

EXAMPLES 6 TO 10

Properties of Microflakes According to Concentrations of Chitosan Solution

In aqueous 3 wt % lactic acid solutions, chitosan which had a viscosity of 116 cps with a deacetylation degree of 94% was dissolved at amounts of 1, 2, 3, 4 and 5 wt %, respectively, and from these chitosan solutions, chitosan microflakes were prepared in the same manner as in Example 1. Microphotographic analysis showed that the microflakes had widths ten or more times as large as their thickness.

Ten chitosan microflakes selected randomly from each of Examples 6 to 10 were measured for dimension and their average values are given in Table 2, below.

TABLE 2

| Properties of Chitosan | Nos. of Examples | | | | |
|---|---|---|---|---|---|
| | 6 | 7 | 8 | 9 | 10 |
| Chitosan Conc. | 1 wt % | 2 wt % | 3 wt % | 4 wt % | 5 wt % |
| Avg. Thick. of Microflakes | 0.8 μm | 1.2 μm | 1.3 μm | 3 μm | 5.3 μm |
| Avg. Width of Microflakes | 10.2 μm | 44 μm | 42 μm | 330 μm | 610 μm |

EXAMPLES 11 TO 13

Properties of Chitosan Microflakes According to Pre-Freezing Temperatures

Chitosan microflakes were prepared in a manner similar to that of Example 1 with the exception that the pre-freezing temperatures were set to be −30° C., −40° C. and −50° C., respectively. The properties of the microflakes according to the pre-freezing temperatures are given in Table 3, below.

TABLE 3

| Condition & Properties | Nos. of Examples | | |
|---|---|---|---|
| | 11 | 12 | 13 |
| Temp. of Pre-Freezing | 30° C. | 40° C. | 50° C. |
| Avg. Thick. of Chitosan Microflakes | 0.9 μm | 1.1 μm | 1.1 μm |
| Avg. Thick. of Chitosan Microflakes | 41 μm | 41 μm | 42 μm |

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A chitosan microflake, which has a plate structure ranging, in thickness, from 0.1 to 10 μm and, in width, from 2 to 2000 μm.

2. The chitosan microflake as set forth in claim 1, wherein the chitosan is deacetylated at 60–99% with a viscosity average molecular weight ranging from 1,000 g/mol to 1,000,000 g/mol.

3. A method for manufacturing a chitosan microflake, comprising the steps of:

dissolving chitosan in a solvent to give a chitosan solution, said solvent being selected from the groups consisting of organic acid solutions, inorganic salt solutions, organic solvents, and mixtures thereof;

freeze-drying the chitosan solution; and pulverizing the freeze-dried chitosan solution to afford a plate structure of a chitosan microflake, which ranges, in thickness, from 0.1 to 10 μm and, in width, from 2 to 2000 μm.

4. The method as set forth in claim 3, wherein said organic acid solutions are composed of acetic acid, lactic acid, citric acid, tartaric acid, malic acid, formic acid, glycolic acid, oxalic acid, succinic acid, ascorbic acid, maleic acid, acrylic acid, gluconic acid, glutamic acid and propionic acid solutions.

* * * * *